United States Patent

Harada et al.

Patent Number: 5,959,105
Date of Patent: Sep. 28, 1999

[54] DIHYDROPERIMIDINE SQUARYLIUM COMPOUND AND MIXTURE OF DIHYDROPERIMIDINE SQUARYLIUM COMPOUNDS

[75] Inventors: Toru Harada; Yoshiharu Yabuki, both of Kanagawa, Japan

[73] Assignee: Fuji Photo Film Co., Ltd., Kanagawa, Japan

[21] Appl. No.: 09/010,121

[22] Filed: Jan. 21, 1998

[30] Foreign Application Priority Data

Jan. 21, 1997 [JP] Japan .................................. 9-009002

[51] Int. Cl.⁶ ..................... C07D 239/70; C07D 487/04; C09B 7/02
[52] U.S. Cl. ..................... 544/231; 544/249; 252/582; 252/587; 359/885; 430/517
[58] Field of Search ..................... 544/249, 231; 252/582, 587

[56] References Cited

U.S. PATENT DOCUMENTS 5,380,635   1/1995   Gomez et al. .......................... 430/517
5,543,086   8/1996   Bertelson et al. ........................ 252/582

*Primary Examiner*—Emily Bernhardt
*Attorney, Agent, or Firm*—Birch, Stewart, Kolasch & Birch, LLP

[57] ABSTRACT

A dihydroperimidine squarylium compound is represented by the formula (I):

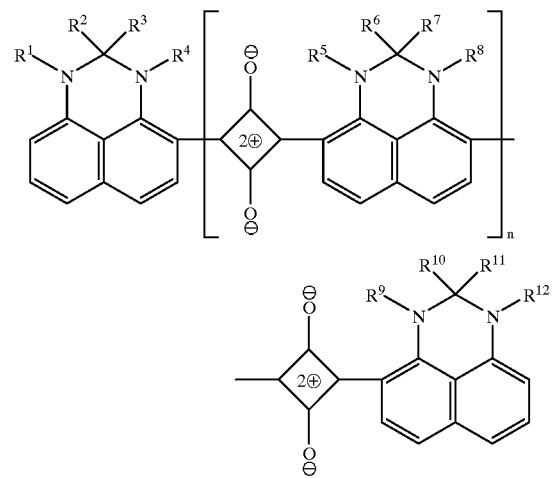

in which each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group, a cycloalkyl group, an aryl group, an aralkyl group, an alkenyl group, an alkynyl group or an acyl group; $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a five- or six-membered nitrogen-containing heterocyclic ring; $R^2$ and $R^3$, $R^6$ and $R^7$ or $R^{10}$ and $R^{11}$ may be combined with each other to form a five- or six-membered aliphatic ring; and n is an integer of 1 to 6. The specification further discloses a mixture of dihydroperimidine squarylium compounds, an infrared absorbing sheet and a silver halide photographic material.

10 Claims, No Drawings

DIHYDROPERIMIDINE SQUARYLIUM COMPOUND AND MIXTURE OF DIHYDROPERIMIDINE SQUARYLIUM COMPOUNDS

FIELD OF THE INVENTION

The present invention relates to a dihydroperimidine squarylium compound, a mixture of dihydroperimidine squarylium compounds, an infrared absorbing sheet and a silver halide photographic material.

BACKGROUND OF THE INVENTION

Dihydroperimidine squarylium dyes are described in J. CHEM. SOC., CHEM. COMMUN., 452–454 (1993) and U.S. Pat. No. 5,380,635. U.S. Pat. No. discloses dyes having the following nucleus:

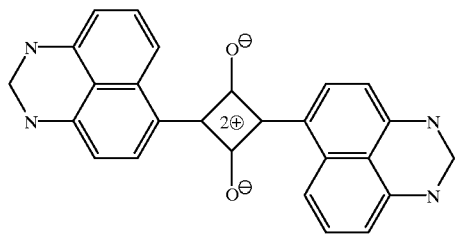

The known dihydroperimidine squarylium dyes have an absorption maximum at a wavelength of about 780 nm to 830 nm. The dihydroperimidine squarylium dyes can be advantageously used as a near infrared filter dye.

A silver halide photographic material is usually processed in an automatic developing machine. The developing machine has a detecting mechanism, which emits an infrared ray to detect insertion of the silver halide photographic material. The mechanism sends a signal of insertion to the developing machine, which then starts development of the photographic material. Recently, it is difficult to detect the insertion, because the amount of silver halide contained in the photogrpahic material tends to be decreased. Japanese Patent Provisional Publication No. 3(1991)-211542 proposes adding a dye having absorption in the infrared region to the photographic material to detect the photogrpahic material. Further, Japanese Patent Application No. 7(1995)-269097 proposes adding solid dispersion of an infrared absorbing dye to the photogrpahic material.

The infrared ray emitted from the detecting mechanism usually has a wavelength of longer than 850 nm. On the other hand, the above-mentioned known dihydroperimidine squarylium compounds have an absorption maximum at not longer than 850 nm. Accordingly, it is not suitable to use the known dihydroperimidine squarylium compounds to detect a photographic material. Further, it is difficult to adjust the absorption maximum of the known dihydroperimidine squarylium compounds.

SUMMARY OF THE INVENTION

An object of the present invention is to provide a dihydroperimidine squarylium compound, which can advantageously be used as an infrared absorbing dye having an appropriate absorption maximum.

Another object of the invention is to provide a mixture of dihydroperimidine squarylium compounds, which can easily adjust the absorption maximum.

A further object of the invention is to provide an infrared absorbing sheet, which contains a dihydroperimidine squarylium compound or a mixture of dihydroperimidine squarylium compounds.

An additional object of the invention is to provide a silver halide photographic material, which contains a dihydroperimidine squarylium compound or a mixture of dihydroperimidine squarylium compounds.

The present invention provides a dihydroperimidine squarylium compound represented by the formula (I):

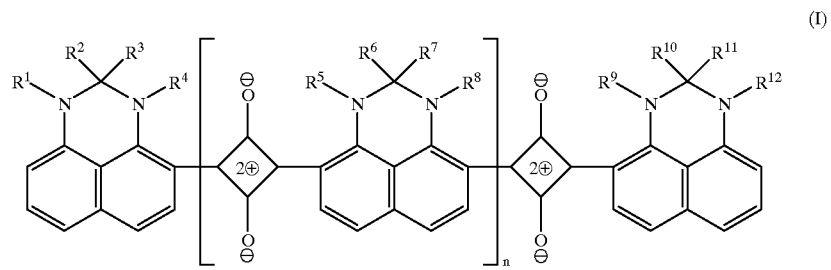

in which each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 20 carbon atoms, a cycloalkyl group having 5 to 12 carbon atoms, an aryl group having 6 to 12 carbon atoms, an aralkyl group having 7 to 12 carbon atoms, an alkenyl group having 2 to 12 carbon atoms, an alkynyl group having 2 to 12 carbon atoms or an acyl group having 2 to 12 carbon atoms; $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a five- or six-membered nitrogen-containing heterocyclic ring; $R^2$ and $R^3$, $R^6$ and $R^7$ or $R^{10}$ and $R^{11}$ may be combined with each other to form a five- or six-membered aliphatic ring; and n is an integer of 1 to 6.

The invention also provides a mixture of dihydroperimidine squarylium compounds represented by the formula (II):

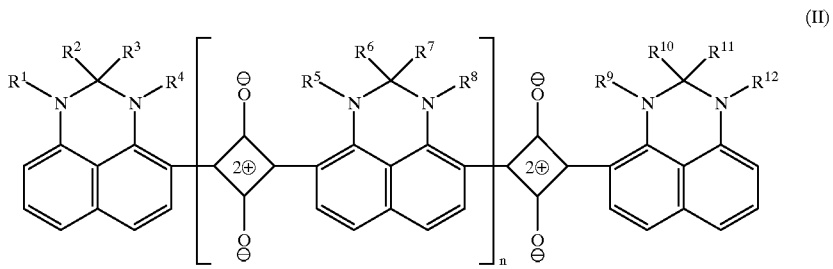

(II)

in which each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 20 carbon atoms, a cycloalkyl group having 5 to 12 carbon atoms, an aryl group having 6 to 12 carbon atoms, an aralkyl group having 7 to 12 carbon atoms, an alkenyl group having 2 to 12 carbon atoms, an alkynyl group having 2 to 12 carbon atoms or an acyl group having 2 to 12 carbon atoms; $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a five- or six-membered nitrogen-containing heterocyclic ring; $R^2$ and $R^3$, $R^6$ and $R^7$ or $R^{10}$ and $R^{11}$ may be combined with each other to form a five- or six-membered aliphatic ring; and the average of n in the mixture is in the range of 1.5 to 3.0.

The invention further provides an infrared absorbing sheet comprising a support and an infrared absorbing layer, wherein the infrared absorbing layer contains the dihydroperimidine squarylium compound represented by the formula (I) or the mixture of the dihydroperimidine squarylium compounds represented by the formula (II).

The invention furthermore provides a silver halide photographic material comprising a support, a silver halide emulsion layer and a non-light-sensitive layer, wherein the silver halide emulsion layer or the non-light-sensitive layer contains the dihydroperimidine squarylium compound represented by the formula (I) or the mixture of the dihydroperimidine squarylium compounds represented by the formula (II).

The maximum absorption of the dihydroperimidine squarylium compound represented by the formula (I) can easily be adjusted by selecting the number of n in the formula (I).

The absorption of the mixture of the dihydroperimidine squarylium compounds represented by the formula (II) can more easily be adjusted by controlling the average of n in the formula (II). Further, the absorption width of the mixture can be made large by widening the range of n in the formula (II).

DETAILED DESCRIPTION OF THE INVENTION

The dihydroperimidine squarylium compound is represented by the formula (I).

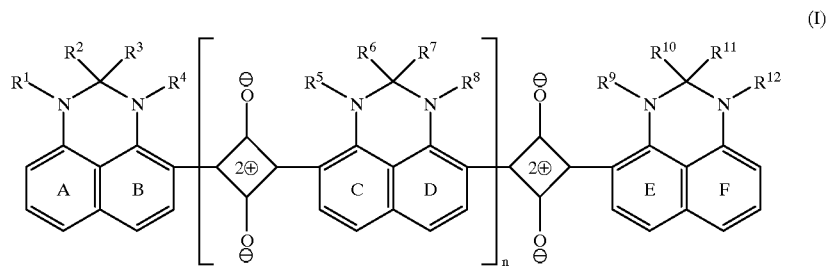

(I)

In the formula (I), each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 20 carbon atoms, a cycloalkyl group having 5 to 12 carbon atoms, an aryl group having 6 to 12 carbon atoms, an aralkyl group having 7 to 12 carbon atoms, an alkenyl group having 2 to 12 carbon atoms, an alkynyl group having 2 to 12 carbon atoms or an acyl group having 2 to 12 carbon atoms. $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a five- or six-membered nitrogen-containing heterocyclic ring. $R^2$ and $R^3$, $R^6$ and $R^7$ or $R^{10}$ and $R^{11}$ may be combined with each other to form a five- or six-membered aliphatic ring.

The alkyl group has 1 to 20 carbon atoms, and preferably has 1 to 12 carbon atoms. Examples of the alkyl groups include methyl, ethyl, propyl, butyl, hexyl and undecyl. The alkyl group may have a substituent group. Examples of the substituent groups include a halogen atom (e.g., F, Cl, Br), an alkoxycarbonyl group (e.g., methoxycarbonyl, ethoxycarbonyl), hydroxyl, an alkoxy group (e.g., methoxy, ethoxy, phenoxy, isobutoxy), carboxyl, sulfo and an acyloxy group (e.g., acetyloxy, butyryloxy, hexyryloxy, benzoyloxy).

The cycloalkyl group has 5 to 12 carbon atoms. Examples of the cycloalkyl groups include cyclopentyl and cyclohexyl. The cycloalkyl group may have a substituent group. Examples of the substituent groups include a halogen atom (e.g., F, Cl, Br), an alkoxycarbonyl group (e.g., methoxycarbonyl, ethoxycarbonyl), hydroxyl, an alkoxy group (e.g., methoxy, ethoxy, phenoxy, isobutoxy), carboxyl, sulfo and an acyloxy group (e.g., acetyloxy, butyryloxy, hexyryloxy, benzoyloxy).

The aryl group has 6 to 12 carbon atoms. Examples of the aryl groups include phenyl and naphthyl. The aryl group may have a substituent group. Examples of the substituent groups include an alkyl group having 1 to 8 carbon atoms (e.g., methyl, ethyl, butyl), an alkoxy group having 1 to 6 carbon atoms (e.g., methoxy, ethoxy), an aryloxy group (e.g., phenoxy, p-chlorophenoxy), a halogen atom (e.g., F, Cl, Br), an alkoxycarbonyl group (e.g., methoxycarbonyl, ethoxycarbonyl), cyano, nitro, sulfo, carboxyl, hydroxyl, amino, an amido group (e.g., acetamido, propionamido) and an acyloxy group (e.g., acetyloxy, butyryloxy).

The aralkyl group has 7 to 12 carbon atoms. Examples of the aralkyl group include benzyl and phenethyl. The aralkyl group may have a substituent group. Examples of the substituent groups include an alkyl group having 1 to 8 carbon atoms (e.g., methyl), an alkoxy group having 1 to 6 carbon atoms (e.g., methoxy) and a halogen atom (e.g., chlorine).

The alkenyl group has 2 to 12 carbon atoms. Examples of the alkenyl groups include 2-pentenyl, 2-butenyl, 1-propenyl and 2-propenyl.

The alkynyl group has 2 to 12 carbon atoms. Examples of the alkynyl groups include ethynyl and 2-propinyl.

The acyl group has 2 to 12 carbon atoms. Examples of the acyl groups include acetyl, propionyl and benzoyl.

The five- or six-membered ring formed by $R^1$ and $R^2$, $R^3$ and $R^4$, $R^5$ and $R^6$, $R^7$ and $R^8$, $R^9$ and $R^{10}$ or $R^{11}$ and $R^{12}$ preferably is a saturated heterocyclic ring. The five- or six-membered ring formed by $R^2$ and $R^3$, $R^6$ and $R^7$ or $R^{10}$ and $R^{11}$ preferably is a saturated aliphatic (cycloalkyl) ring.

In the formula (I), each of the benzene rings A, B, C, D, E and F may have a substituent group. Examples of the substituent groups include an alkyl group having 1 to 8 carbon atoms (e.g., methyl, ethyl, butyl), an alkoxy group having 1 to 6 carbon atoms (e.g., methoxy, ethoxy), an aryloxy group (e.g., phenoxy, p-chlorophenoxy), a halogen atom (e.g., F, Cl, Br), an alkoxycarbonyl group (e.g., methoxycarbonyl, ethoxycarbonyl), cyano, nitro, sulfo, carboxyl, hydroxyl, amino, an amido group (e.g., acetamido, propionamido) and an acyloxy group (e.g., acetyloxy, butyryloxy).

In the formula (I), n is an integer of 1 to 6.

The mixture of the dihydroperimidine squarylium compounds is represented by the formula (II).

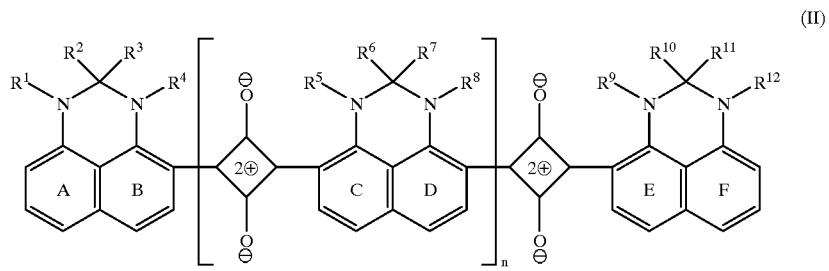

In the formula (II), $R^1, R^2, R^3, R^4, R^5, R^6, R^7, R^8, R^9, R^{10}, R^{11}, R^{12}$, and the benzene rings A, B, C, D, E and F have the same meanings as those defined in the formula (I).

In the formula (II), the average of n in the mixture is in the range of 1.5 to 3.0. The number of n of each compounds contained in the mixture preferably is an integer of 0 to 6, and more preferably is an integer of 0 to 4. Examples of the combinations of the number n in the mixture include 0 and 1, 1 and 2, 2 and 3, 3 and 4, 0, 1 and 2, 1, 2 and 3, 0, 1, 2, and 3 and 0, 1, 2, 3 and 4.

Examples of the dihydroperimidine squarylium compounds are shown below.

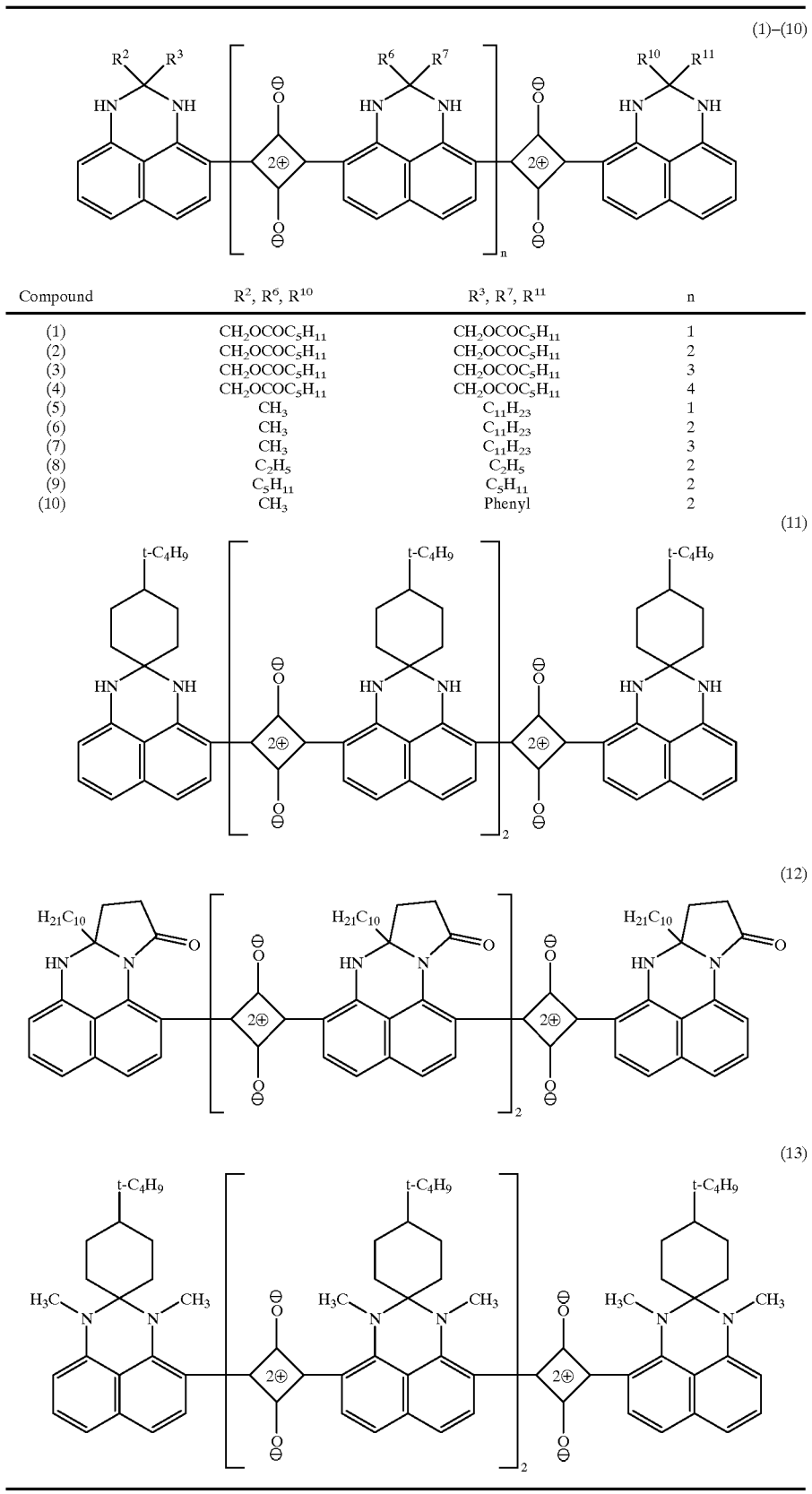
| Compound | R², R⁶, R¹⁰ | R³, R⁷, R¹¹ | n |
|---|---|---|---|
| (1) | CH₂OCOC₅H₁₁ | CH₂OCOC₅H₁₁ | 1 |
| (2) | CH₂OCOC₅H₁₁ | CH₂OCOC₅H₁₁ | 2 |
| (3) | CH₂OCOC₅H₁₁ | CH₂OCOC₅H₁₁ | 3 |
| (4) | CH₂OCOC₅H₁₁ | CH₂OCOC₅H₁₁ | 4 |
| (5) | CH₃ | C₁₁H₂₃ | 1 |
| (6) | CH₃ | C₁₁H₂₃ | 2 |
| (7) | CH₃ | C₁₁H₂₃ | 3 |
| (8) | C₂H₅ | C₂H₅ | 2 |
| (9) | C₅H₁₁ | C₅H₁₁ | 2 |
| (10) | CH₃ | Phenyl | 2 |

Examples of the mixtures of the dihydroperimidine squarylium compounds are shown below.

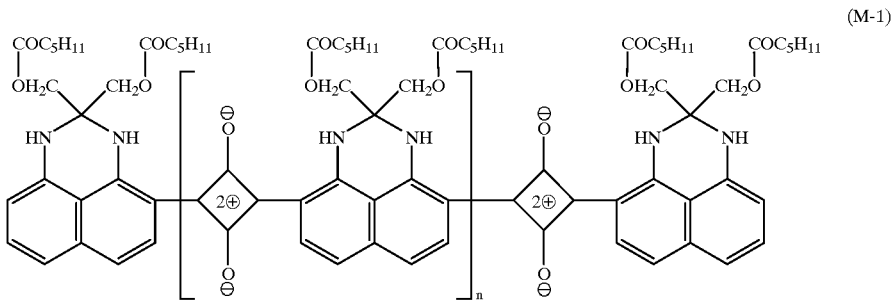

(M-1)

(n: 0, 1, 2, 3 and 4, the average of n: 2.2)

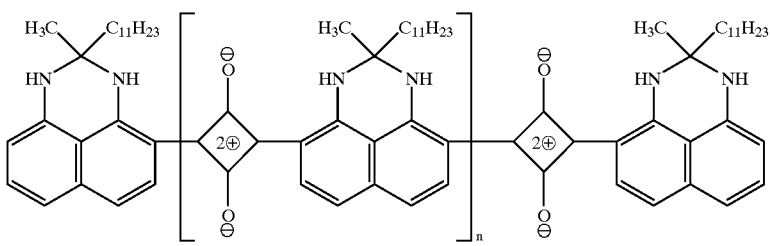

(M-2)

(n: 0, 1, 2, 3 and 4, the average of n: 2.2)

The dihydroperimidine squarylium compound or the mixture can be used in various materials.

For example, the dihydroperimidine squarylium compound or the mixture can be added to a thermal fixing acceleration type toner. The fixing reaction of the toner can be accelerated by absorbing infrared light. Further, the compound or the mixture can be added to an electrophotographic photoreceptor. A recently disclosed electrophotographic process using infrared light. Furthermore, the compound or the mixture can be used as a sensitizer for photopolymerization or photo-crosslinking reaction. A recent photo chemical reaction proposes using infrared light while a conventional photo chemical reaction usually uses ultraviolet light.

A solution or dispersion of the dihydroperimidine squarylium compound or the mixture can be used as an infrared absorbing ink (or paint). An invisible image can be formed by using the infrared absorbing ink. The infrared absorbing paint can be used as an anti-reflection material for a laser beam. Further, the infrared absorbing ink can be used in an optical recording material (e.g., optical disc). Furthermore, the infrared absorbing paint can be used as an infrared photo sensor.

A solution or dispersion of the dihydroperimidine squarylium compound or the mixture can be coated on a support to prepare an infrared absorbing sheet. The sheet can be used as a filter, such as a band pass filter, an optical filter or a heat-absorbing filter. Further, the infrared absorbing sheet can be used in a plasma display panel (PDP), which emits infrared light. The emitted infrared light disturbs a remote controller, which also uses infrared light. The infrared absorbing sheet can be attached to the front surface of the plasma display panel to shield the infrared light.

The infrared absorbing filter, ink and paint are described in Japanese Patent Provisional Publication Nos. 58(1983)-1762 and 64(1989)-69686.

The dihydroperimidine squarylium compound or the mixture can also be added to a silver halide photographic material, which comprises a support, a silver halide emulsion layer and a non-light-sensitive layer. The compound or the mixture in the silver halide photographic material can function as a filter dye, an antihalation dye or an antiirradiation dye. The compound or the mixture can also be used to detect a silver halide photographic material by an infrared detecting mechanism of an automatic developing machine. The compound or the mixture can be added to the silver halide emulsion layer or the non-light-sensitive layer. The non-light-sensitive layer preferably contains the compound or the mixture.

A silver halide photographic material containing an infrared dye is described in Japanese Patent Application No. 7(1995)-269097 and Japanese Patent Provisional Publication No. 3(1991)-211542.

EXAMPLE 1

The dihydroperimidine squarylium compounds and mixtures can be synthesized according to the following formulas. The value for n can be adjusted by the amount of squaric acid.

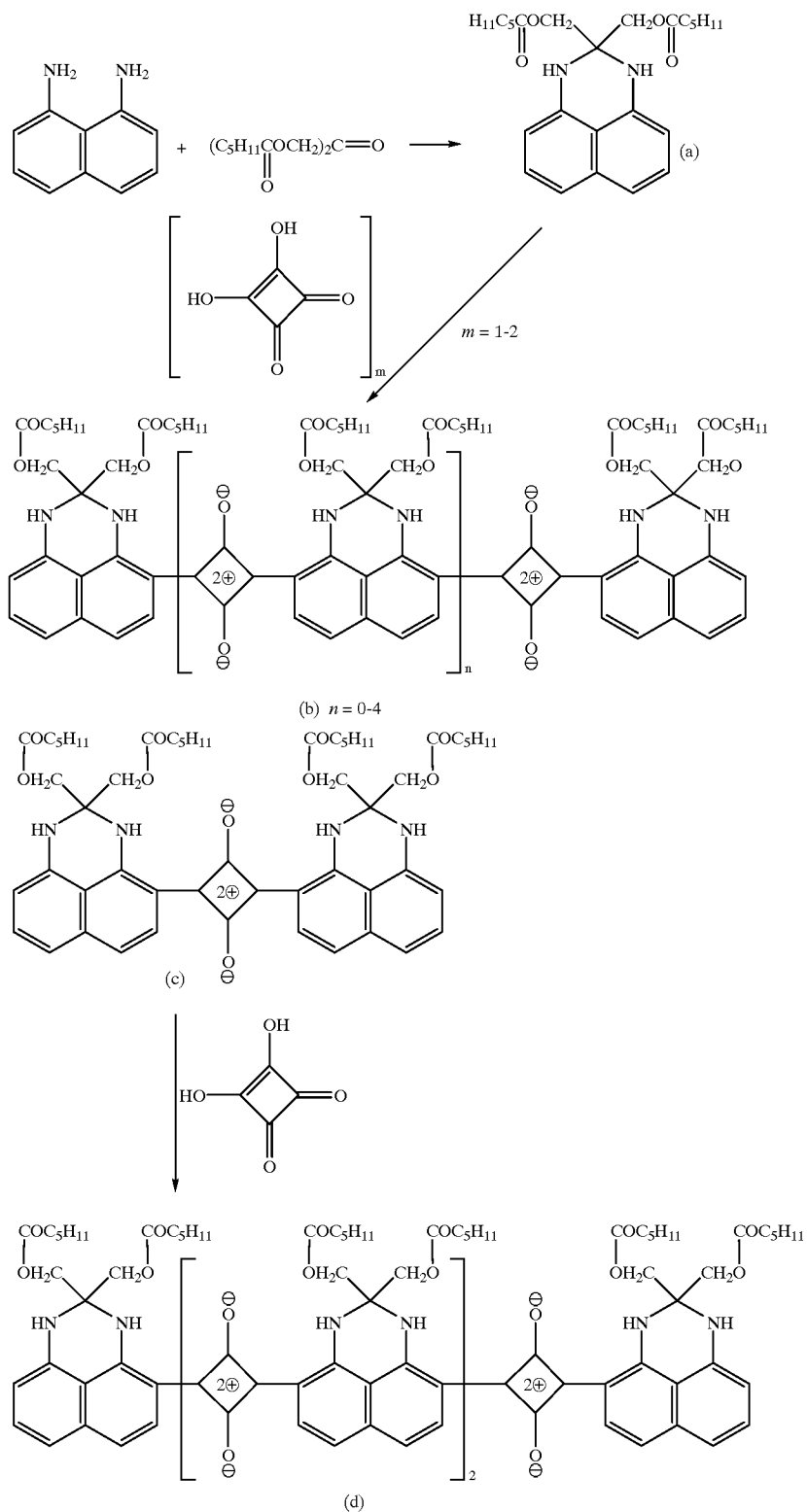

Synthesis of Compound (1)

In a steam bath, 39.6 g of 1,8-diaminonaphthalene, 71.5 g of dipentylcarbonyloxymethyl ketone and 30 mg of sodium p-toluenesulfonate monohydrate were stirred for 3 hours under heating. To the mixture, 150 ml of methyl alcohol was added. The crystals precipitated were filtered to obtain 97.3 g of 2,2-dipentylcarbonyloxymethyl-2,3-dihydroperimidine (a).

A mixture of 2.13 g of 2,2-dipentylcarbonyloxymethyl-2,3-dihydroperimidine (a) obtained above, 0.57 g of squaric acid, 10 ml of n-butyl alcohol and 10 ml of toluene was heated at an external temperature of 130° C. for 5 hours with removing water evolved. To the mixture, 20 ml of methyl alcohol was added. The crystals precipitated were separated by filtration. Then, the crystals were subjected to column chromatography using silica gel and chloroform to obtain the compound (1).

yield: 0.5 g, λmax: 948.2 nm (acetone), $\epsilon$: $2.19 \times 10^5$

Synthesis of Compound (2)

A mixture of 17.5 g of 2,2-dipentylcarbonyloxymethyl-2,3-dihydroperimidine (a) obtained above, 2.1 g of squaric acid, 100 ml of n-butanol and 100 ml of toluene was heated at an external temperature of 130° C. for 3 hours with removing water evolved. After the mixture was allowed to stand for cooling, 50 ml of methyl alcohol was added. The crystals precipitated were filtered and then subjected to column chromatography using silica gel and chloroform to obtain 8.9 g of the compound (c).

A mixture of 3.2 g of the compound (c) obtained above, 0.178 g of squaric acid, 30 ml of n-butanol and 30 ml of toluene was heated at an external temperature of 140° C. To the mixture, 30 ml of acetone was added. The crystals precipitated were separated by filtration and then subjected to recrystallization from methylene chloride/acetone to obtain the compound (2).

yield: 0.55 g, λmax: 1070.5 nm ($CH_2Cl_2$), $\epsilon$: $1.69 \times 10^5$

Synthesis of Mixture (M-2)

A mixture of 84.5 g of 2-methyl-2-undecyl-2,3-dihydroperimidine, 22.3 g of squaric acid, 500 ml of n-butanol and 500 ml of toluene was stirred at an external temperature of 140° C. for 4 hours. The crystals precipitated were separated by filtration and then washed with acetone to obtain 50 g of the mixture (M-2).

λmax ($\epsilon$: relative value based on the absorbance in case of n=0 being 1)

810 nm (1.0), 991.6 nm (1.25), 1120.4 nm (1.36), 1200 nm (0.9), solvent=$CH_2Cl_2$ Other compounds and mixtures were synthesized in a manner similar. The values of amax are set forth in Table 1.

TABLE 1

| Compound or mixture | λmax ($CH_2Cl_2$) |
| --- | --- |
| (1) | 948 nm |
| (2) | 1070 nm |
| (3) | 1160 nm |
| (4) | 1230 |
| (M-1) | 798, 949, 1072, 1162 nm |
| (5) | 992 nm |
| (6) | 1120 nm |

TABLE 1-continued

| Compound or mixture | λmax ($CH_2Cl_2$) |
| --- | --- |
| (7) | 1200 nm |
| (M-2) | 810, 992, 1120, 1200 nm |

EXAMPLE 2

Preparation of Infrared Absorbing Sheet

To 10 g of the compound (1) weighed out, 11.5 g of tricresyl phosphate (high boiling point organic solvent) was added, and further 24 ml of chloroform was added to dissolve the compound. The solution was emulsified in a 10 wt. % gelatin aqueous solution containing 1.5 g of sodium dodecylbenzenesulfonate. To the emulsion, a 10 wt. % gelatin aqueous solution was added so that a layer (filter layer) of the resulting emulsion had the following composition. Then, the emulsion was coated on a triacetyl cellulose film support having been provided with a subbing layer, to form a filter layer (an infrared absorbing layer). Separately, a 10 wt. % gelatin aqueous solution was added to 1 g of sodium 2,4-dichloro-6-hydroxy-s-triazine so that a layer (protective layer) of the resulting solution had the following composition. Then, the solution was coated on the filter layer to form a protective layer. Thus, a sample No. 001 was prepared.

| Filter layer | |
| --- | --- |
| Compound (1) | 0.2 g/m$^2$ |
| Tricresyl phosphate | 1.0 g/m$^2$ |
| Gelatin | 3.8 g/m$^2$ |
| Protective layer | |
| Sodium 2,4-dichloro-6-hydroxy-s-triazine | 0.1 g/m$^2$ |
| Gelatin | 1.8 g/m$^2$ |

Sample Nos. 002 to 004 were prepared in the same manner as in the preparation of the sample No. 001, except that the compound (1) was replaced with each of the compound (2), the comparative compounds (a) and (b) in an equimolar amount. Each of the resulting samples was divided into two parts, and one was allowed to stand for 3 days under the conditions of a temperature of 60° C. and a relative humidity of 70%, while the other was allowed to stand for 2 days under irradiation with a light of a fluorescent lamp of 20,000 lux. Then, the density was measured. From the percentage of the measured density to the density before the discoloration test, a ratio of the residual dye was determined. The results are set forth in Table 2.

(Comparative compound a)

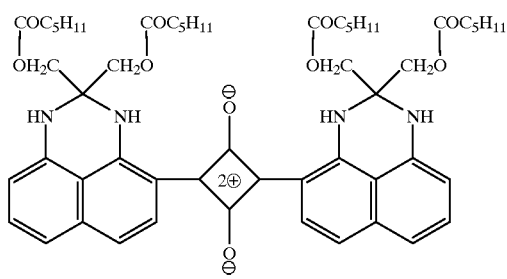

(Comparative compound b)

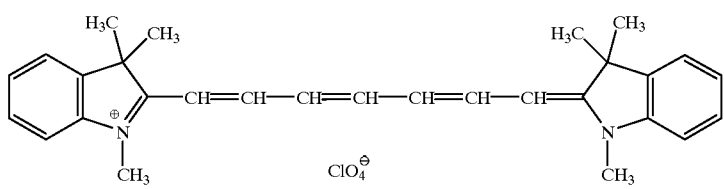

TABLE 2

| Sample No. | Compound | Ratio of remaining dye *1 (%) | Ratio of remaining dye *2 (%) |
|---|---|---|---|
| 001 | (1) | 90 | 92 |
| 002 | (2) | 90 | 93 |
| 003 | (a) | 80 | 85 |
| 004 | (b) | 50 | 30 |

(Remark)
Ratio of remaining dye *1: under forced conditions of high temperature and high humidity
Ratio of remaining dye *2: under forced conditions of strong light From the results set forth in Table 2, it has been confirmed that the compounds according to the present invention are stable.

EXAMPLE 3
Preparation of Silver Halide Emulsion

To 820 cc of water, 3 g of sodium chloride, gelatin (average molecular weight: 20,000) and 0.04 g of 4-aminopyrazolo[3,4-d]pyrimidine (Tokyo Kasei K.K.) were added. To the resulting solution maintained at 55° C., an aqueous solution containing 10.0 g of silver nitrate and an aqueous solution containing 5.61 g of potassium bromide and 0.72 g of potassium chloride were added by a double jet method over a period of 30 minutes with stirring. Then, an aqueous solution containing 20 g of gelatin (having been treated with alkali and hydrogen peroxide) and 6 g of potassium chloride was added. The mixture was allowed to stand for 25 minutes. Then, an aqueous solution containing 155 g of silver nitrate and an aqueous solution containing 87.3 g of potassium bromide and 21.9 g of potassium chloride were added by a double jet method over a period of 58 minutes. The flow rate during the addition was increased in such a manner that the flow rate at the time of completion of the addition became 3 times as much as the flow rate at the time of starting of the addition.

Further, an aqueous solution containing 5 g of silver nitrate and an aqueous solution containing 2.7 g of potassium bromide, 0.6 g of sodium chloride and 0.013 g of $K_4FE(CN)_6$ were added by a double jet method over a period of 3 minutes. Thereafter, the temperature of the system was lowered to 35° C., and the soluble salts were removed by a sedimentation method. The temperature of the system was raised to 40° C. Then, 28 g of gelatin, 0.4 g of zinc nitrate and 0.051 g of benzoisothiazolone were added, and the mixture was adjusted to pH 6.0 with sodium hydroxide. Thus, silver halide grains, in which not less than 80% (based on the projected area) of the whole grains were grains having an aspect ratio of not less than 3, were obtained. The silver halide grains had an average diameter (based on the projected area) of 0.85 μm, an average thickness of 0.151 μm and a silver chloride content of 20 mol %.

After the temperature of the system was raised to 56° C., 0.002 mol (in terms of silver) of silver iodide grains (average grain size: 0.05 μm) were added with stirring. Then, 4.8 mg of sodium ethylthiosulfinate, 520 mg of the following sensitizing dye and 112 mg of 4-hydroxy-6-methyl-1,3,3a,7-tetrazaindene were added. Further, 1.8 mg of chloroauric acid, 100 mg of potassium thiocyanate, 1.8 mg of sodium thiosulfate pentahydrate and 2.15 mg of the following selenium compound were added. The mixture was subjected to chemical ripening for 50 minutes and rapidly cooled to obtain a silver halide emulsion.

(Sensitizing dye)

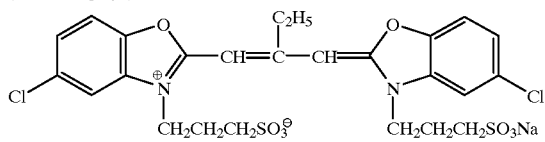

(Selenium compound)

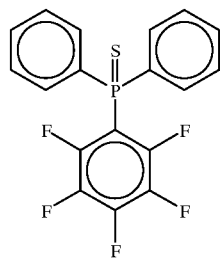

To the silver halide emulsion, the following additives were added in the following amounts per 1 mol of the silver halide to prepare a coating solution for forming a silver halide emulsion layer.

| Silver halide emulsion layer (coating amount in terms of silver: 1.25 g/m²) | |
|---|---|
| 2,6-Bis(hydroxyamino)-4-diethylamino-1,3,5-triazine | 80 mg |
| Sodium polyacrylate (average molecular weight: 41,000) | 4.0 g |
| Compound B | 9.7 g |
| Ethyl acrylate/acrylic acid/methacrylic acid copolymer (plasticizer, copolymerization ratio = 95/2/3) | 20.0 g |
| Nitron | 50 mg |
| Compound C | 5.0 mg |
| Gelatin (total coating weight in the emulsion layer) | 1.2 g/m² |

(Compound B)

[structure: benzene ring with OH, OH, and SO$_3$Na substituents]

(Compound C)

[structure: dichlorobenzimidazole with two C$_2$H$_5$ groups and =CH—CH=N—phenyl substituent]

Preparation of Silver Halide Photographic Material

Both surfaces of a polyethylene terephthalate film, each of which was provided with a subbing layer, were coated with the coating solutions for the silver halide emulsion layer (shown above) and the surface protective layer (shown below) to prepare a silver halide photographic material.

| Surface protective layer | |
|---|---|
| Gelatin | 0.61 g/m² |
| Dextran (average molecular weight: 39,000) | 0.61 g/m² |
| Sodium polyacrylate (average molecular weight: 41,000) | 70 mg/m² |
| 1,2-Bis(sulfonylacetamide)ethane (hardener) | 56 mg/m² |
| Particles of polymethyl methacrylate/methacrylic acid copolymer (matting agent, copolymerization ratio = 9/1, average particle diameter: 3.5 μm) | 0.06 g/m² |
| 4-Hydroxy-6-methyl-1,3,3a,7-tetrazaindene | 15.5 mg/m² |
| Coating aid I | 13 mg/m² |
| Coating aid II | 45 mg/m² |
| Coating aid III | 6.5 mg/m² |
| Coating aid IV | 3 mg/m² |
| Coating aid V | 1 mg/m² |
| Coating aid VI | 1.7 mg/m² |
| Coating aid VII | 100 mg/m² |

(Coating aid I)

C$_8$H$_{17}$—[phenyl]—(OCH$_2$CH$_2$)$_3$—SO$_3$Na (Coating aid II)

C$_{16}$H$_{33}$O—(CH$_2$CH$_2$O)$_{10}$—H (Coating aid III)

C$_{17}$H$_{33}$CO—N(CH$_3$)—CH$_2$CH$_2$SO$_3$Na (Coating aid IV)

C$_8$H$_{17}$SO$_2$—N(C$_3$H$_7$)—(CH$_2$CH$_2$O)$_{16}$—H (Coating aid V)

C$_8$H$_{17}$SO$_2$—N(C$_3$H$_7$)—(CH$_2$CH$_2$O)$_4$—(CH$_2$)$_4$—SO$_3$Na (Coating aid VI)

[structure: tetrazole with SH group linked to phenyl–COONa]

(Coating aid VII)

[structure: benzene ring with OH, OH, and Cl substituents]

In the above preparation of the photographic material, the dye shown in Table 3 was incorporated into the surface protective layer. The coating weight of the dye was 25 mg/m².

Evaluation of Photographic Material

For each samples, 10 films were inserted into an automatic processing machine (remodeled FPM-9000, Fuji Photo Film Co., Ltd.) through a film insertion opening to evaluate the number of the detected sheets (samples). This automatic processing machine is provided with a mechanism, which has one infrared emitting element (GL-514, Sharp Corporation) and one infrared receiving element (PT501, Sharp Corporation) at the film insertion opening and has a function of starting a roller conveyer to automatically convey a film sample to a developing tank when an infrared radiation is blocked by the insertion of the film sample.

TABLE 3

| Sample No. | Compound or mixture | Number of detected sheets |
|---|---|---|
| 201 | (1) | 10 |
| 202 | (M-1) | 10 |
| 203 | (M-2) | 10 |
| 204 | (a) | 3 |
| 205 | (b) | 2 |

From the results set forth in Table 3, it has been confirmed that the photographic materials according to the present invention can easily be detected with an infrared ray.

We claim:

1. A dihydroperimidine squarylium compound represented by the formula

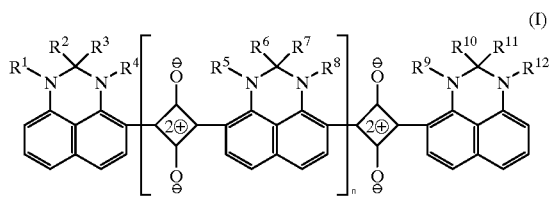

(I)

in which each of $R^1$, $R^2$, $R^3$, $R^4$, $R^5$, $R^6$, $R^7$, $R^8$, $R^9$, $R^{10}$, $R^{11}$ and $R^{12}$ is hydrogen, an alkyl group having 1 to 20 carbon atoms, a cycloalkyl group having 5 to 12 carbon atoms, an aryl group having 6 to 12 carbon atoms, an aralkyl group having 7 to 12 carbon atoms, an alkenyl group having 2 to 12 carbon atoms, an alkynyl group having 2 to 12 carbon atoms or an acyl group having 2 to 12 carbon atoms; $R^1$ and $R^2$, $R^3$ and $R^4$, $R^5$ and $R^6$, $R^7$ and $R^8$, $R^9$ $R^{10}$ or $R^{11}$ and $R^{12}$ may be combined with each other to form a pyrrolidone ring; $R^2$ and $R^3$, $R^6$ and $R^7$ or $R^{10}$ and $R^{11}$ may be combined with each other to form a five- or six-membered aliphatic ring, and n is an integer of 1 to 6;

wherein when the alkyl group is substituted, the substituents are selected from the group consisting of a halogen atom, an alkoxycarbonyl group, hydroxyl, an alkoxy groups, carboxyl, sulfo and an acyloxy group, wherein when the cycloalkyl group is substituted, the substituents are selected from the group consisting of a halogen atom, an alkoxycarbonyl group, hydroxyl, an alkoxy group, carboxyl, sulfo and an acyloxy group, wherein when the aryl group is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl, hydroxyl, amino, an amido group and an acyloxy group, wherein when the aralkyl group is substituted, the substituents are selected from the group consisting of an alkyl group having 1 to 8 carbon atoms, an alkoxy group having 1 to 6 carbon atoms and a halogen atom, wherein when the benzene ring shown in the formula is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl, hydroxyl, amino, an amido group and an acyloxy group.

2. The dihydroperimidine squarylium compound as claimed in claim 1, wherein each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 12 carbon atoms, a cycloalkyl group having 5 to 12 carbon atoms, an aryl group having 6 to 12 carbon atoms or an acyl group having 2 to 12 carbon atoms;

wherein when the alkyl group is substituted, the substituents are selected from the group consisting of a halogen atom, an alkoxycarbonyl group, hydroxyl, an alkoxy group, carboxyl, sulfo and an acyloxy group, wherein when the cycloalkyl group is substituted, the substituents are selected from the group consisting of a halogen atom, an alkoxycarbonyl group, hydroxyl, an alkoxy group, carboxyl, sulfo and an acyloxy group, wherein when the aryl group is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl, hydroxyl, amino, an amido group and an acyloxy group.

3. The dihydroperimidine squarylium compound as claimed in claim 1, wherein each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 12 carbon atoms which is optionally substituted with an acyloxy group, or an aryl group having 6 to 12 carbon atoms, and n is an integer of 1 to 6.

4. The dihydroperimidine squarylium compound as claimed in claim 3, wherein each of $R^1$, $R^4$, $R^5$, $R^8$, $R^9$, and $R^{12}$ is hydrogen; and each of $R^2$, $R^3$, $R^6$, $R^7$, $R^{10}$ and $R^{11}$ are independently $CH_2OCOC_5H_{11}$, $CH_3$, $CH_2H_5$, $C_5H_{11}$, $C_{11}H_{23}$, or phenyl, and n is an integer of 1 to 4.

5. The dihydroperimidine squarylium compound as claimed in claim 1, wherein each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, or an alkyl group having 1 to 20 carbon atoms; $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a pyrrolidone ring; $R^2$ and $R^3$, $R^6$ and $R^7$ or $R^{10}$ and $R^{11}$ may be combined with each other to form a five- or six-membered aliphatic ring, and n is an integer of 1 to 6.

6. The dihydroperimidine squarylium compound as claimed in claim 5, which is selected from the group consisting of

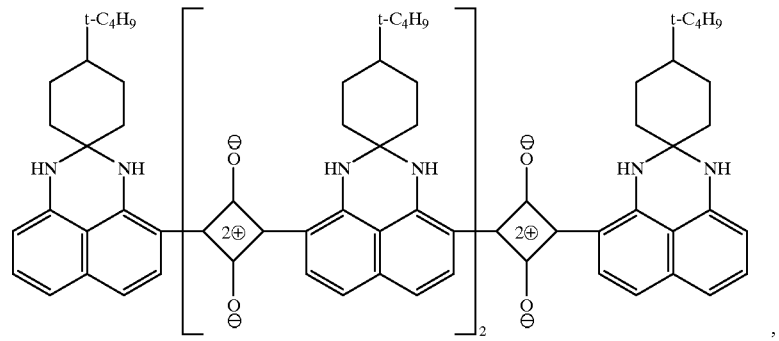

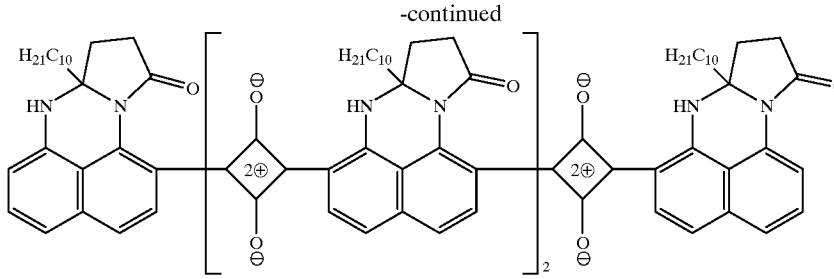

, and

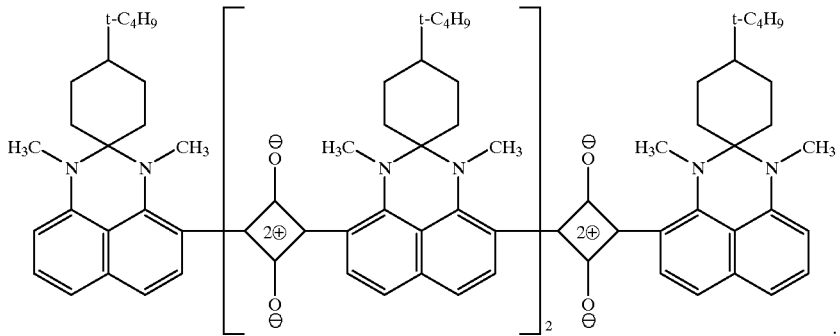

7. A mixture of dihydroperimidine squarylium compounds represented by the formula (II):

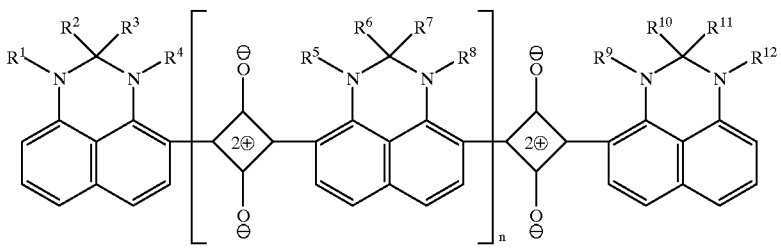

(II)

in which each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 20 carbon atoms, a cycloalkyl group having 5 to 12 carbon atoms, an aryl group having 6 to 12 carbon atoms, an aralkyl group having 7 to 12 carbon atoms, an alkenyl group having 2 to 12 carbon atoms, an alkynyl group having 2 to 12 carbon atoms or an acyl group having 2 to 12 carbon atoms; $R^1$ and $R^2$, $R^3$ and $R^4$, $R^5$ and $R^6$, $R^7$ and $R^8$, $R^9$ and $R^{10}$ or $R^{11}$ and $R^{12}$ may be combined with each other to form a pyrrolidone ring; $R^2$ and $R^3$, $R^6$ and $R^7$ or $R^{10}$ and $R^{11}$ may be combined with each other to form a five- or six-membered aliphatic ring; and the average of n in the mixture is in the range of 1.5 to 3.0;

wherein when the alkyl group is substituted, the substituents are selected from the group consisting of a halogen atom, an alkoxycarbonyl group, hydroxyl, an alkoxy group, carboxyl, sulfo and an acyloxy group, wherein when the cycloalkyl group is substituted, the substituents are selected from the group consisting of a halogen atom, an alkoxycarbonyl group, hydroxyl, an alkoxy group, carboxyl, sulfo and an acyloxy group, wherein the aryl group is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl, hydroxyl, amino, an amido group and an acyloxy group, wherein when the aralkyl group is substituted, the substituents are selected from the group consisting of an alkyl group having 1 to 8 carbon atoms, an alkoxy group having 1 to 6 carbon atoms and a halogen atom, wherein when the benzene ring shown in the formula is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl hydroxyl, amino, an amido group and an acyloxy group.

8. The mixture as claimed in claim 7, wherein each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 12 carbon atoms, a cycloalkyl group having 5 to 12 carbon atoms, an aryl group having 6 to 12 carbon atoms or an acyl group having 2 to 12 carbon atoms;

wherein when the alkyl group is substituted, the substituents are selected from the group consisting of a halogen atom, an alkoxycarbonyl group, hydroxyl, an alkoxy group, carboxyl, sulfo and an acyloxy group, wherein when the cycloalkyl group is substituted, the substituents are selected from the group consisting of a halogen atom, an alkoxycarbonyl group, hydroxyl, an alkoxy group, carboxyl, sulfo and an acyloxy group, wherein when the aryl group is substituted, the substituents are selected from the group consisting of an alkyl group having 1 to 8 carbon atoms, an alkoxy group having 1 to 6 carbon atoms, an aryloxy group, a halogen atom, an alkoxycarbonyl group, cyano, nitro, sulfo, carboxyl, hydroxyl, amino, an amido group and an acyloxy group.

9. The mixture of dihydroperimidine squarylium compounds as claimed in claim 7, wherein each of $R^1$, $R^2$, $R^3$, $R^4$, $R^5$, $R^6$, $R^7$, $R^8$, $R^9$, $R^{10}$, $R^{11}$ and $R^{12}$ independently is hydrogen, an alkyl group having 1 to 12 carbon atoms which is optionally substituted with an acyloxy group, or an aryl group having 6 to 12 carbon atoms, and the average of n in the mixture is in the range of 1.5 to 3.0.

10. The mixture of dihydroperimidine squarylium compounds as claimed in claim 9, wherein each of $R^1$, $R^4$, $R^5$, $R^8$, $R^9$, and $R^{12}$ is hydrogen; and each of $R^2$, $R^3$, $R^6$, $R^7$, $R^{10}$ and $R^{11}$ are independently $CH_2OCOC_5H_{11}$, $CH_3$, or $C_{11}H_{23}$, and the average of n in the mixture is in the range of 1.5 to 3.0.

* * * * *